(12) United States Patent
Meyer et al.

(10) Patent No.: US 12,731,673 B2
(45) Date of Patent: Sep. 8, 2026

(54) PATIENT AND CONSUMER DATA DE-IDENTIFICATION

(71) Applicant: Align Technology, Inc., San Jose, CA (US)

(72) Inventors: Eric P. Meyer, Zurich (CH); Christopher E. Cramer, Durham, NC (US); Doruk Cetin, Zurich (CH); Niko Benjamin Huber, Zug (CH); Chad Clayton Brown, Cary, NC (US)

(73) Assignee: Align Technology, Inc., San Jose, CA (US)

( * ) Notice: Subject to any disclaimer, the term of this patent is extended or adjusted under 35 U.S.C. 154(b) by 331 days.

(21) Appl. No.: 18/140,196

(22) Filed: Apr. 27, 2023

(65) Prior Publication Data

US 2023/0352150 A1 Nov. 2, 2023

Related U.S. Application Data

(60) Provisional application No. 63/336,832, filed on Apr. 29, 2022.

(51) Int. Cl.
*G16H 30/40* (2018.01)
*G16H 10/60* (2018.01)

(52) U.S. Cl.
CPC ............ *G16H 30/40* (2018.01); *G16H 10/60* (2018.01)

(58) Field of Classification Search
None
See application file for complete search history.

(56) References Cited

U.S. PATENT DOCUMENTS 5,975,893 A 11/1999 Chishti et al.
6,227,850 B1 5/2001 Chishti et al.
6,227,851 B1 5/2001 Chishti et al.
6,299,440 B1 10/2001 Phan et al.
(Continued)

FOREIGN PATENT DOCUMENTS

EP 3451209 B1 * 8/2020 ......... G06F 21/6254

OTHER PUBLICATIONS

Wen et. al., IdentityDP: Differential Private Identification Protection for Face Images, IEEE International Conference on Visual Communications and Image Processing, 2020; Published Mar. 2, 2021 (Year: 2021).*

(Continued)

*Primary Examiner* — Anne-Marie K Alderson
(74) *Attorney, Agent, or Firm* — Lowenstein Sandler LLP

(57) ABSTRACT

The present technology provides solutions for anonymizing patient data and in particular, for anonymizing potentially unique patient-identifying information while retaining clinically relevant information, for example, that can be used to illustrate the results or outcomes of a clinical intervention. In some aspects, a process of the disclosed technology can include steps for receiving patient data, wherein the patient data comprises a patient image corresponding with a patient, receiving treatment data, wherein the treatment data is based on a treatment goal for the patient, automatically determining, using one or more semantic controls, one or more anonymization parameters for the patient image; and generating, based on the one or more anonymization parameters, an anonymized patient image. Systems and machine-readable media are also provided.

26 Claims, 7 Drawing Sheets

(56) References Cited

U.S. PATENT DOCUMENTS 6,318,994 B1 11/2001 Chishti et al.
6,371,761 B1 4/2002 Cheang et al.
6,386,878 B1 5/2002 Pavlovskaia et al.
6,406,292 B1 6/2002 Chishti et al.
6,409,504 B1 6/2002 Jones et al.
6,457,972 B1 10/2002 Chishti et al.
6,488,499 B1 12/2002 Miller
6,514,074 B1 2/2003 Chishti et al.
6,554,611 B2 4/2003 Chishti et al.
6,582,229 B1 6/2003 Miller et al.
6,602,070 B2 8/2003 Miller et al.
6,621,491 B1 9/2003 Baumrind et al.
6,688,886 B2 2/2004 Hughes et al.
6,726,478 B1 4/2004 Isiderio et al.
6,729,876 B2 5/2004 Chishti et al.
6,739,869 B1 5/2004 Taub et al.
6,767,208 B2 7/2004 Kaza
6,783,360 B2 8/2004 Chishti
7,040,896 B2 5/2006 Pavlovskaia et al.
7,063,532 B1 6/2006 Jones et al.
7,074,038 B1 7/2006 Miller
7,074,039 B2 7/2006 Kopelman et al.
7,077,647 B2 7/2006 Choi et al.
7,108,508 B2 9/2006 Hedge et al.
7,134,874 B2 11/2006 Chishti et al.
7,156,661 B2 1/2007 Choi et al.
7,160,107 B2 1/2007 Kopelman et al.
7,241,142 B2 7/2007 Abolfathi et al.
7,293,988 B2 11/2007 Wen
7,309,230 B2 12/2007 Wen
7,357,634 B2 4/2008 Knopp
7,555,403 B2 6/2009 Kopelman et al.
7,637,740 B2 12/2009 Knopp
7,689,398 B2 3/2010 Cheng et al.
7,736,147 B2 6/2010 Kaza et al.
7,746,339 B2 6/2010 Matov et al.
7,844,356 B2 11/2010 Matov et al.
7,844,429 B2 11/2010 Matov et al.
7,865,259 B2 1/2011 Kuo et al.
7,878,804 B2 2/2011 Korytov et al.
7,880,751 B2 2/2011 Kuo et al.
7,904,308 B2 3/2011 Arnone et al.
7,930,189 B2 4/2011 Kuo
7,942,672 B2 5/2011 Kuo
7,970,627 B2 6/2011 Kuo et al.
7,970,628 B2 6/2011 Kuo et al.
8,038,444 B2 10/2011 Kitching et al.
8,044,954 B2 10/2011 Kitching et al.
8,075,306 B2 12/2011 Kitching et al.
8,092,215 B2 1/2012 Stone-Collonge et al.
8,099,268 B2 1/2012 Kitching et al.
8,108,189 B2 1/2012 Chelnokov et al.
8,126,726 B2 2/2012 Matov et al.
8,260,591 B2 9/2012 Kass et al.
8,275,180 B2 9/2012 Kuo
8,401,826 B2 3/2013 Cheng et al.
8,439,672 B2 5/2013 Matov et al.
8,562,338 B2 10/2013 Kitching et al.
8,591,225 B2 11/2013 Wu et al.
8,788,285 B2 7/2014 Kuo
8,843,381 B2 9/2014 Kuo et al.
8,874,452 B2 10/2014 Kuo
8,896,592 B2 11/2014 Boltunov et al.
8,930,219 B2 1/2015 Trosien et al.
9,037,439 B2 5/2015 Kuo et al.
9,060,829 B2 6/2015 Sterental et al.
9,125,709 B2 9/2015 Matty
9,211,166 B2 12/2015 Kuo et al.
9,220,580 B2 12/2015 Borovinskih et al.
9,364,296 B2 6/2016 Kuo
9,375,300 B2 6/2016 Matov et al.
9,414,897 B2 8/2016 Wu et al.
9,492,245 B2 11/2016 Sherwood et al.
9,642,678 B2 5/2017 Kuo
10,248,883 B2 4/2019 Borovinskih et al.
10,342,638 B2 7/2019 Kitching et al.
10,463,452 B2 11/2019 Matov et al.
10,595,966 B2 3/2020 Carrier, Jr. et al.
10,617,489 B2 4/2020 Grove et al.
10,722,328 B2 7/2020 Velazquez et al.
10,758,322 B2 9/2020 Pokotilov et al.
10,779,718 B2 9/2020 Meyer et al.
10,792,127 B2 10/2020 Kopelman et al.
10,817,622 B2 * 10/2020 Rosenberg ............. G16H 15/00
10,828,130 B2 11/2020 Pokotilov et al.
10,835,349 B2 11/2020 Cramer et al.
10,973,611 B2 4/2021 Pokotilov et al.
10,996,813 B2 5/2021 Makarenkova et al.
10,997,727 B2 5/2021 Xue et al.
11,020,205 B2 6/2021 Li et al.
11,020,206 B2 6/2021 Shi et al.
11,026,766 B2 6/2021 Chekh et al.
11,033,359 B2 6/2021 Velazquez et al.
11,071,608 B2 7/2021 Derakhshan et al.
11,096,763 B2 8/2021 Akopov et al.
11,116,605 B2 9/2021 Nyukhtikov et al.
11,147,652 B2 10/2021 Mason et al.
11,151,753 B2 10/2021 Gao et al.
11,154,381 B2 10/2021 Roschin et al.
11,259,896 B2 3/2022 Matov et al.
11,357,598 B2 6/2022 Cramer
11,395,717 B2 7/2022 Yuryev et al.
11,432,908 B2 9/2022 Kopelman et al.
11,436,191 B2 * 9/2022 Kuo ....................... G06Q 10/10
11,464,604 B2 10/2022 Makarenkova et al.
11,478,334 B2 10/2022 Matov et al.
11,484,389 B2 11/2022 Sterental et al.
11,521,732 B2 12/2022 Levin et al.
11,534,272 B2 12/2022 Li et al.
11,553,988 B2 1/2023 Mednikov et al.
11,633,268 B2 4/2023 Moalem et al.
11,642,195 B2 5/2023 Gao et al.
11,651,494 B2 5/2023 Brown et al.
11,654,001 B2 5/2023 Roschin et al.
11,687,671 B2 * 6/2023 Venkataraman .... G06F 21/6254 726/26
11,776,680 B2 * 10/2023 Simhadri ................ G06T 7/246
2003/0008259 A1 1/2003 Kuo et al.
2003/0143509 A1 7/2003 Kopelman et al.
2003/0207227 A1 11/2003 Abolfathi
2004/0137400 A1 7/2004 Chishti et al.
2004/0152036 A1 8/2004 Abolfathi
2004/0197728 A1 10/2004 Abolfathi et al.
2004/0259049 A1 12/2004 Kopelman et al.
2005/0182654 A1 8/2005 Abolfathi et al.
2005/0244791 A1 11/2005 Davis et al.
2006/0127836 A1 6/2006 Wen
2006/0127852 A1 6/2006 Wen
2006/0127854 A1 6/2006 Wen
2006/0275731 A1 12/2006 Wen et al.
2006/0275736 A1 12/2006 Wen et al.
2007/0128573 A1 * 6/2007 Kuo ......................... A61C 7/08 433/24
2008/0306724 A1 12/2008 Kitching et al.
2010/0009308 A1 1/2010 Wen et al.
2010/0068672 A1 3/2010 Arjomand et al.
2010/0068676 A1 3/2010 Mason et al.
2010/0092907 A1 4/2010 Knopp
2010/0167243 A1 7/2010 Spiridonov et al.
2013/0204599 A1 8/2013 Matov et al.
2016/0310235 A1 10/2016 Derakhshan et al.
2017/0273760 A1 9/2017 Morton et al.
2018/0280118 A1 10/2018 Cramer
2019/0272387 A1 * 9/2019 Gkoulalas-Divanis ...................... G06F 21/604
2019/0328487 A1 10/2019 Levin et al.
2019/0328488 A1 10/2019 Levin et al.
2019/0378607 A1 * 12/2019 Chen ................... G06F 21/6254
2020/0155274 A1 5/2020 Pimenov et al.
2020/0297458 A1 9/2020 Roschin et al.
2020/0306011 A1 10/2020 Chekhonin et al.
2020/0306012 A1 10/2020 Roschin et al.
2020/0373002 A1 * 11/2020 Kadambi ............... G16H 30/40
2021/0134436 A1 5/2021 Meyer et al.

(56) References Cited

U.S. PATENT DOCUMENTS

| | | | | |
|---|---|---|---|---|
| 2021/0174477 | A1 | 6/2021 | Shi et al. | |
| 2021/0224424 | A1* | 7/2021 | Blumhofer | G06F 21/6254 |
| 2021/0312595 | A1* | 10/2021 | Simhadri | G16H 50/70 |
| 2022/0391537 | A1* | 12/2022 | Gotthardt | H04W 12/02 |
| 2023/0409749 | A1* | 12/2023 | Li | H04N 21/4318 |
| 2024/0028762 | A1* | 1/2024 | Chaudhry | G06F 3/0482 |

OTHER PUBLICATIONS

Roberts EA, Troiano C, Spiegel JH. Standardization of guidelines for patient photograph deidentification. Annals of plastic surgery. Jun. 1, 2016;76(6):611-4.

* cited by examiner

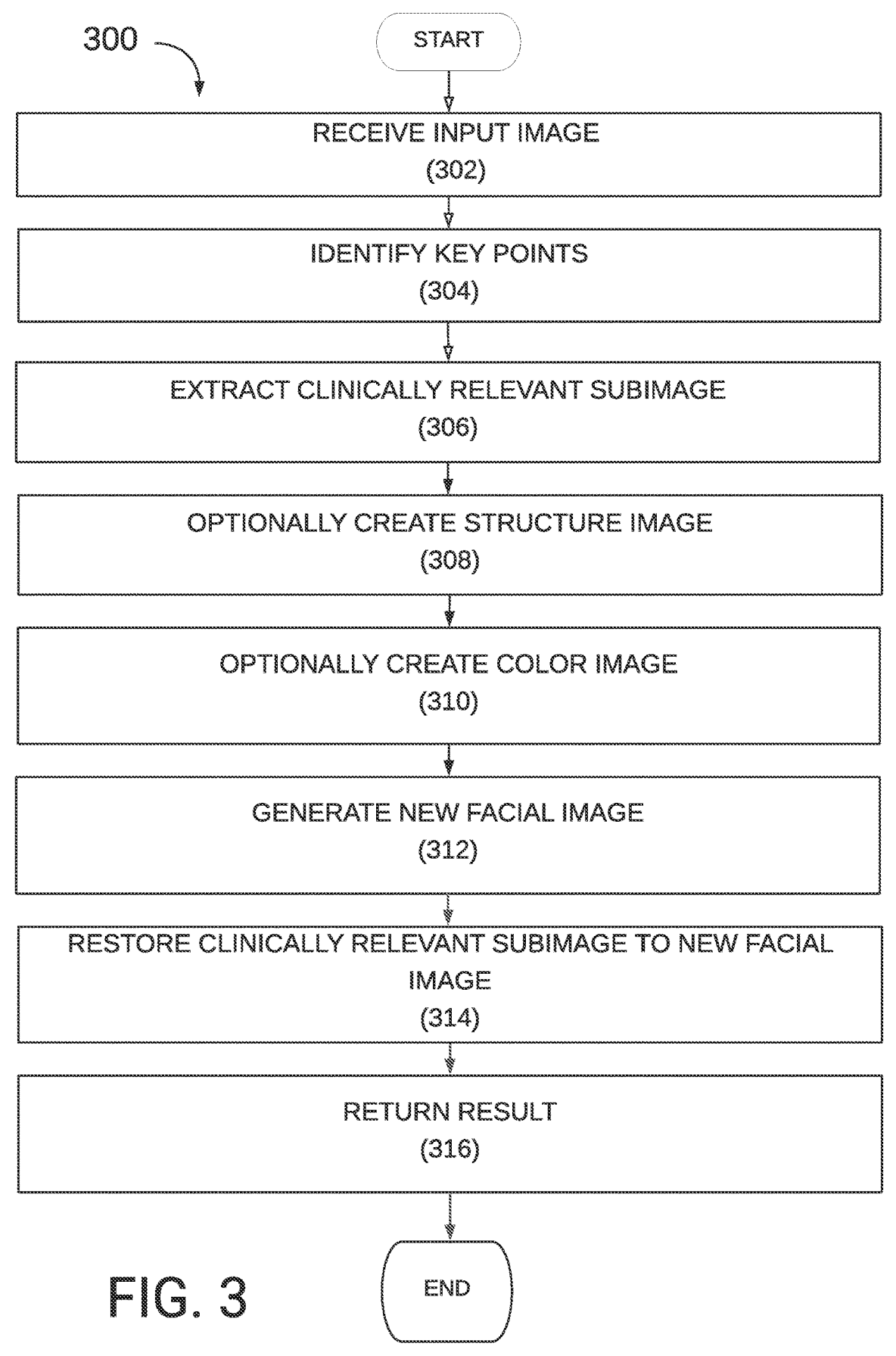

300

START

RECEIVE INPUT IMAGE (302)

IDENTIFY KEY POINTS (304)

EXTRACT CLINICALLY RELEVANT SUBIMAGE (306)

OPTIONALLY CREATE STRUCTURE IMAGE (308)

OPTIONALLY CREATE COLOR IMAGE (310)

GENERATE NEW FACIAL IMAGE (312)

RESTORE CLINICALLY RELEVANT SUBIMAGE TO NEW FACIAL IMAGE (314)

RETURN RESULT (316)

END

FIG. 3

400
425
122
430
420
432
435
437
440
Generative Adversarial Network
455
459
457
455
460

PATIENT AND CONSUMER DATA DE-IDENTIFICATION

RELATED APPLICATIONS

This patent application claims the benefit under 35 U.S.C. § 119(e) of U.S. Provisional Application No. 63/336,832, filed Apr. 29, 2022.

TECHNICAL FIELD

The present technology provides solutions for anonymizing patient data and in particular, for anonymizing or obfuscating potentially unique patient-identifying features while retaining clinically relevant information, for example, that can be used to illustrate the results or outcomes of a clinical intervention to other clinical professionals.

BACKGROUND

Conventional approaches to removing personally identifying patient information from confidential patient data can be less than ideal in at least some respects. Many countries require that medical records comply with standards to protect patient data, such as the Health Insurance Portability and Accountability Act ("HIPAA") in the United States and the General Data Protection Regulations ("GDPR") in the European Union. These standards can require that personally identifiable information be removed prior to making patient data, such as patient images, publicly available. Treatment professionals such as physicians may wish to share treatment information with other professionals in order to disseminate knowledge with respect to patient care and best practices. In order to present such patient data to third-parties, personally identifiable information is typically removed. However, conventional approaches to remove identifying features/artifacts can result in less than complete patient images and images that appear unnatural or aesthetically unappealing.

SUMMARY

Various example implementations are summarized. These example implementations are merely for illustration and should not be construed as limiting.

In a first implementation, a computer-implemented method comprises: receiving patient data, wherein the patient data comprises a patient image corresponding with a patient; receiving treatment data, wherein the treatment data is based on a treatment goal for the patient; automatically determining, using one or more semantic controls, one or more anonymization parameters for the patient image; and generating, based on the one or more anonymization parameters, an anonymized patient image.

A second implementation may further extend the first implementation. In the second implementation, the anonymized patient image preserves a clinically relevant portion of the patient image based on the treatment data.

A third implementation may further extend the first or second implementation. In the third implementation, the one or more anonymization parameters are based on the treatment data.

A fourth implementation may further extend any of the first through third implementations. In the fourth implementation, the one or more anonymization parameters are based on the patient data.

A fifth implementation may further extend any of the first through fourth implementations. In the fifth implementation, the one or more anonymization parameters for the patient image specify one or more anonymization regions in the patient image that are to be modified to obfuscate an identity of the patient.

A sixth implementation may further extend any of the first through fifth implementations. In the sixth implementation, the one or more anonymization parameters for the patient image specify one or more clinically relevant regions in the patient image that are not to be modified.

A seventh implementation may further extend any of the first through sixth implementations. In the seventh implementation, the one or more anonymization parameters specify one or more image characteristics to be applied to generate the anonymized patient image.

An eighth implementation may further extend the seventh implementation. In the eighth implementation, the one or more image characteristics include color parameters, blur filter parameters, geometric parameters, or a combination thereof.

A ninth implementation may further extend any of the first through eighth implementations. In the ninth implementation, the one or more semantic controls are based on a user input.

In a tenth implementation, a system comprises: at least one memory; and at least one processor coupled to the at least one memory, the at least one processor configured to: receive patient data, wherein the patient data comprises a patient image corresponding with a patient; receive treatment data, wherein the treatment data is based on a treatment goal for the patient; automatically determine, using one or more semantic controls, one or more anonymization parameters for the patient image; and generate, based on the one or more anonymization parameters, an anonymized patient image.

An 11$^{th}$ implementation may further extend the tenth implementation. In the 11$^{th}$ implementation, the anonymized patient image preserves a clinically relevant portion of the patient image based on the treatment data.

A 12$^{th}$ implementation may further extend the tenth or 11$^{th}$ implementation. In the 12$^{th}$ implementation, the one or more anonymization parameters are based on the treatment data.

A 13$^{th}$ implementation may further extend any of the tenth through 12$^{th}$ implementations. In the 13$^{th}$ implementation, the one or more anonymization parameters are based on the patient data.

A 14$^{th}$ implementation may further extend any of the tenth through 13$^{th}$ implementations. In the 14$^{th}$ implementation, the one or more anonymization parameters for the patient image specify one or more anonymization regions in the patient image that are to be modified to obfuscate an identity of the patient.

A 15$^{th}$ implementation may further extend any of the tenth through 14$^{th}$ implementations. In the 15$^{th}$ implementation, the one or more anonymization parameters for the patient image specify one or more clinically relevant regions in the patient image that are not to be modified.

A 16$^{th}$ implementation may further extend any of the tenth through 15$^{th}$ implementations. In the 16$^{th}$ implementation, the one or more anonymization parameters specify one or more image characteristics to be applied to generate the anonymized patient image.

A 17$^{th}$ implementation may further extend the 16$^{th}$ implementation. In the 17$^{th}$ implementation, the one or more image characteristics include color parameters, blur filter parameters, geometric parameters, or a combination thereof.

An 18$^{th}$ implementation may further extend any of the tenth through 17$^{th}$ implementations. In the 18$^{th}$ implementation, the one or more semantic controls are based on a user input.

In a 19$^{th}$ implementation, a non-transitory computer-readable storage medium comprising at least one instruction for causing a computer or processor to: receive patient data, wherein the patient data comprises a patient image corresponding with a patient; receive treatment data, wherein the treatment data is based on a treatment goal for the patient; automatically determine, using one or more semantic controls, one or more anonymization parameters for the patient image; and generate, based on the one or more anonymization parameters, an anonymized patient image.

A 20$^{th}$ implementation may further extend the 19$^{th}$ implementation. In the 20$^{th}$ implementation, the anonymized patient image preserves a clinically relevant portion of the patient image based on the treatment data.

A 21$^{st}$ implementation may further extend the 19$^{th}$ or 20$^{th}$ implementations. In the 21$^{st}$ implementation, the one or more anonymization parameters are based on the treatment data.

A 22$^{nd}$ implementation may further extend any of the 19$^{th}$ through 21$^{st}$ implementations. In the 22$^{nd}$ implementation, the one or more anonymization parameters are based on the patient data.

A 23$^{rd}$ implementation may further extend any of the 19$^{th}$ through 22$^{nd}$ implementations. In the 23$^{rd}$ implementation, the one or more anonymization parameters for the patient image specify one or more anonymization regions in the patient image that are to be modified to obfuscate an identity of the patient.

A 24$^{th}$ implementation may further extend any of the 19$^{th}$ through 23$^{rd}$ implementations. In the 24$^{th}$ implementation, the one or more anonymization parameters for the patient image specify one or more clinically relevant regions in the patient image that are not to be modified.

A 25$^{th}$ implementation may further extend any of the 19$^{th}$ through 24$^{th}$ implementations. In the 25$^{th}$ implementation, the one or more anonymization parameters specify one or more image characteristics to be applied to generate the anonymized patient image.

A 26$^{th}$ implementation may further extend any of the 19$^{th}$ through 25$^{th}$ implementations. In the 26$^{th}$ implementation, the one or more image characteristics include color parameters, blur filter parameters, geometric parameters, or a combination thereof.

A 27$^{th}$ implementation may further extend any of the 19$^{th}$ through 26$^{th}$ implementations. In the 27$^{th}$ implementation, the one or more semantic controls are based on a user input.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIGS. 2 and 3 illustrate conceptual block diagrams of processes for using semantic controls to anonymize patient data, in accordance with some examples.

DESCRIPTION OF EXAMPLE EMBODIMENTS

Figure 1:
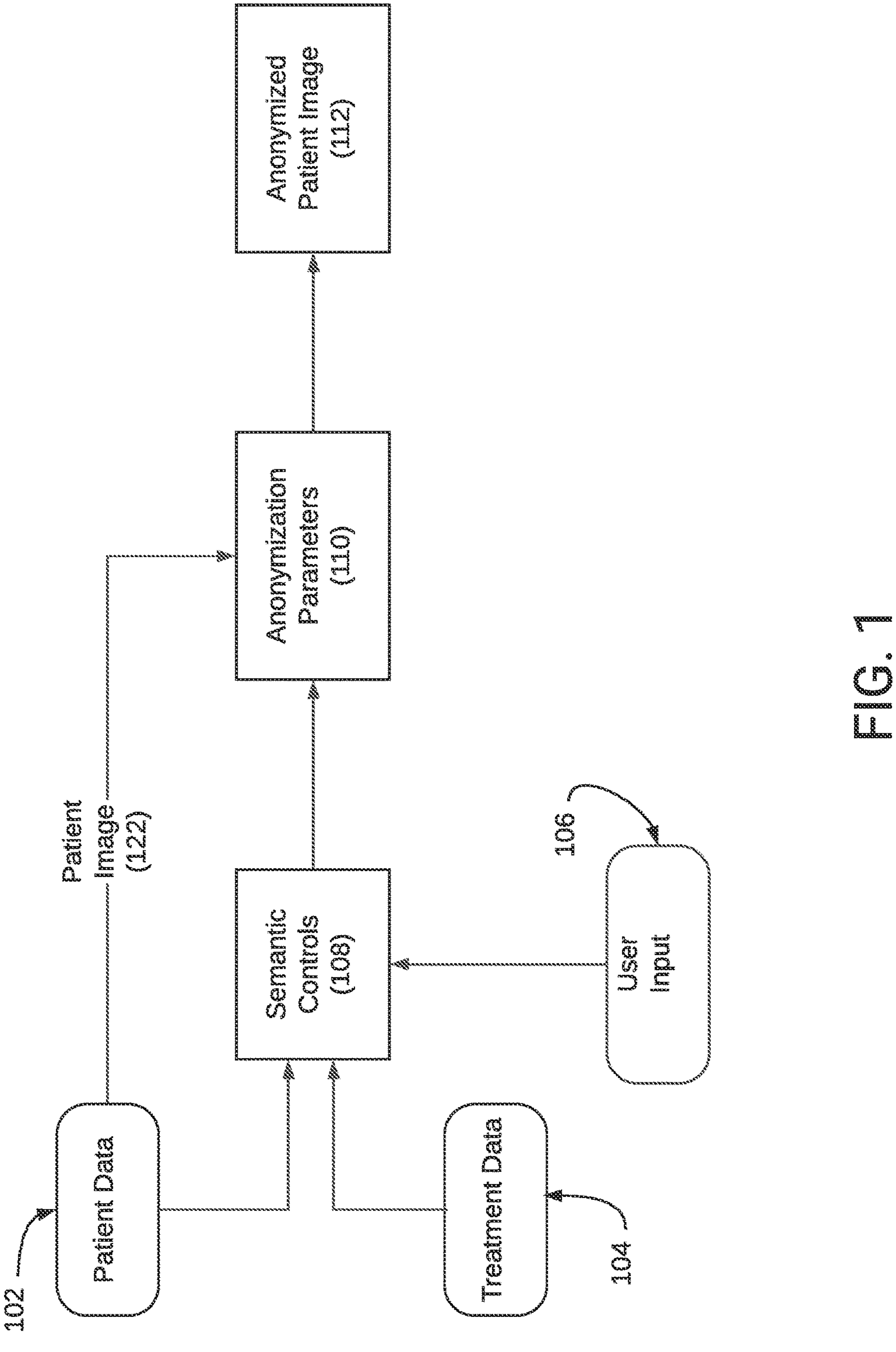
FIG. 1 illustrates a conceptual block diagram of an example system for anonymizing patient data using one or more semantic controls, in accordance with some examples.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Overview

In some aspects, a computer-implemented method of the disclosed technology can include receiving patient (or customer/consumer) data, wherein the patient data comprises a patient image corresponding with a patient; receiving treatment data, wherein the treatment data is based on a treatment goal for the patient; automatically determining, using one or more semantic controls, one or more anonymization parameters for the patient image; and generating, based on the one or more anonymization parameters, an anonymized patient image.

A system of the disclosed technology can include at least one memory, and at least one processor coupled to the at least one memory, the at least one processor configured to: receive patient data, wherein the patient data comprises a patient image corresponding with a patient; receive treatment data, wherein the treatment data is based on a treatment goal for the patient; automatically determine, using one or more semantic controls, one or more anonymization parameters for the patient image; and generate, based on the one or more anonymization parameters, an anonymized patient image.

A non-transitory computer-readable storage medium can include at least one instruction for causing a computer or processor to receive patient data, wherein the patient data comprises a patient image corresponding with a patient; receive treatment data, wherein the treatment data is based on a treatment goal for the patient; automatically determine, using one or more semantic controls, one or more anonymization parameters for the patient image; and generate, based on the one or more anonymization parameters, an anonymized patient image.

Description

Prior to performing a medical treatment, a medical professional may record or otherwise capture patient data, that includes visual data (e.g., image data, video data, or 3D video scan data) of a patient's anatomy, including one or more clinically relevant areas. For example, before the administration of treatment, a medical professional may take pictures or three-dimensional (3D) scans, e.g., cone-beam computed tomography (CBCT) scans, of the patient's mouth and/or face. In some instances, the treatment professional may wish to confer with other professionals (e.g., specialists such as orthodontists, oral surgeons, aesthetic surgeons, periodontists, and/or general dentists, etc.) over possible treatment approaches or present case studies publicly. The treatment professional may share the pictures of the patient with other treatment professionals and/or other patients to discuss treatments. To preserve patient privacy, it may be desirable to keep certain patient data, such as patient-identifiable information, from other treatment professionals. Additionally, some regulations and laws may require privacy standards regarding patient information as noted above. However, some data, such as photos showing the patient's face, may be fundamentally identifiable.

Conventionally, patient images may be rendered unidentifiable by masking, blanking or otherwise obscuring portions of patients' faces, such as eyes and noses. For example, a portion of the patients' faces such as the eyes can be blacked out. Alternatively, the patient images may be cropped to remove patient-identifiable features. Although effective in maintaining patient anonymity, these blacked out or cropped images may be aesthetically unattractive and, may distract from the clinical conditions, and may obscure potentially relevant clinical information.

Aspects of the present disclosure, provide solutions for anonymizing patient data to preserve patient privacy in a manner that results in aesthetically cohesive patient outcome imaging i.e., that retains clinically relevant treatment information, for example, that may be useful for sharing amongst colleagues or other professionals and/or patients. In some aspects, the manner in which patient information is anonymized (or obfuscated) can be performed using one or more semantic controls, for example, that can be based on patient data, treatment data, and/or user provided input. As used herein, semantic controls can include rule-bases systems, or applications (computer program code), that can be used to automate and/or systematize modifications to patient imaging, e.g., to produce anonymized patient image data. In some aspects, semantic controls can be used to determine or identify a set of anonymization parameters, for example, that can be used to apply or implement specific image editing operations to produce a resulting anonymized patient image. As discussed in further detail below, semantic controls can be configured to receive various types of information, including but not limited to patient data that includes patient imaging, treatment data comprising information about the treatment to be administered to the patient, and/or user input data that can include inputs provided by a clinician or other treatment professional.

In practice, semantic controls can be used to automatically determine how patient data, such as patient imagery, should be modified to obfuscate or remove potentially identifying or unique information. Patient imagery, such as image data (photographs, videos, 3D videos) or 3D scan data (e.g., which may be intraoral scan data generated by an intraoral scanner or x-ray data such as CBCT data), can be included in patient data, and may be consumed or operated on by one or more semantic controls to help determine the manner in which patient imagery should be modified for anonymization purposes. As used herein, patient data may include other information about a patient, such as demographic information (e.g., sex, age, height, etc.).

Determinations made about how to optimally anonymize patient data (e.g., patient imagery) can be made based on treatment data corresponding with the patient. As used herein, treatment data can include virtually any information relating to a potential clinical intervention associated with the patient. Examples of treatments include orthodontic treatment, prosthodontic treatment, plastic surgery, cosmetic dental treatment, weight gain, weight loss, and so on. In some examples, treatment data can be used by the semantic controls to automatically determine anonymization parameters that should be applied to the patient imagery, e.g., to anonymize the patient imagery, such as photographs and/or 3D scans. As discussed in further detail below, treatment data can be used to determine anonymization parameters that define portions of a patient image that should be modified to obfuscate the patient's identity (e.g., image anonymization regions), and/or to identify portions of the patient image that should remain unchanged, for example, to preserve any clinically relevant information that may be of use for sharing between clinical professionals and/or other patients/consumers, etc. Additionally, anonymization parameters may indicate image-wide changes, e.g., that are not limited to specific pixel regions. By way of example, anonymization parameters may indicate overall changes to image color tone or hue (e.g., to alter the patient's skin color), image geometry or the prominence of specific image regions or features, e.g., to change or obfuscate the patient's gender identity, etc. Several of the provided examples discuss clinical interventions in an orthodontic context, however it is understood that the disclosed aspects may be applied in other clinical settings and are not limited to the examples provided herein.

FIG. 1 illustrates a conceptual block diagram of an example system 100 for anonymizing patient data using one or more semantic controls. As illustrated in the example of system 100, patient data 102, treatment data 104, and/or user input 106 can all be exposed to semantic controls 108. As discussed above, semantic controls can include a set of rules (or models) that can be configured to generate anonymization parameters 110 to define how an image (e.g., a patient image) can be modified to remove potentially patient identifying information or features. For example, semantic controls 108 may include one or more models (e.g., trained machine learning models or rule-based systems (e.g., implemented as applications or other program code), to automatically identify image editing changes (anonymization parameters 110), that can be applied to generate an anonymized patient image 112, for example, that obfuscates the patient's identity, but retains clinically relevant information about the patient's procedure.

As indicated in the example of FIG. 1, a patient image can be provided as patient data 102. As such, the system 100 can be configured to automatically apply anonymization parameters 110 to a received patient image (in patient data 102), and to output the generated anonymized patient image 112. As discussed in further detail below, the resulting anonymization parameters 110 can be based on the semantic controls 108, and the combination of patient data 102, treatment data 104, and/or user input 108 that are exposed to the semantic controls 108.

In some examples, semantic controls 108 can determine/generate anonymization parameters 110 based on patient data 102. By way of example, the patient data 102 may be used to identify specific image characteristics and/or image regions that should be modified and/or preserved. For instance, patient data may be determined to reveal specific characteristics of a patient that may be used to identify the patient, and therefore that should be obfuscated or removed via the application of specific anonymization parameters 110. By way of example, patient imaging may be analyzed to determine that certain image properties should be modified e.g., to obfuscate a race or gender of the patient, and/or to remove (or alter) potentially identifying features, such as skin blemishes, or the like. In this example, anonymization parameters 110 may indicate specific changes to colors, tones or hues, of the received patient image. Additionally, the anonymization parameters may define specific pixel areas or regions (e.g., anonymization regions) that are to be altered, as well as specific pixel areas/regions that are to remain unaltered (e.g., clinically relevant image regions), in order to preserve the clinical significance of the resulting anonymized patient image 112.

In some examples, semantic controls 108 can determine/generate anonymization parameters 110 based on treatment data 104. By way of example, the treatment data 104 may be used to identify details about a specific clinical intervention associated with the patient. For instance, treatment data 104 may be used to identify specific regions of the patient's anatomy (e.g., areas of the face, teeth, and/or jaw) that are to be modified by a clinical treatment, and therefore that should be preserved via the application of specific anonymization parameters 110. In some aspects, treatment data 104 may be used by the semantic controls 108 to identify particularly salient features of the post treatment outcome, e.g., that should be preserved in the resulting anonymized patient image 112. By way of example, orthodontic treatments may result in anonymization parameters 110 that are configured to preserve artifacts related to the movement or repositioning of one or more teeth and/or jaw positions, as opposed to preserving the geometry of other facial regions, such as the nose and/or eyes etc. As discussed in further detail below, the anonymization parameters 110 can be used to define specific image anonymization regions (e.g., that are altered or otherwise obfuscated), and/or clinically relevant image regions (e.g., that remain unaltered in order to convey relevant details of the applied clinical intervention.

In some examples, semantic controls 108 can determine/generate anonymization parameters 110 based on user input data 106. By way of example, user inputs 106 may be provided (e.g., by a clinician or other professional) to specific aspects of the patient image 122 that should either be modified (e.g., for anonymization), or that should be preserved/maintained, e.g., to convey specific details of the clinical outcome. In effect, the user input data 106 may provide explicit controls that can be used by the clinician to alter or tune the anonymization parameters 110, in order to generate an anonymized patient image 112 that captures relevant clinical details, without losing important clinical details. By way of example, user input 106 may be used by a clinician to alter the patient image 122 in a manner that is more relevant to a particular audience or patient demographic.

Figure 2:
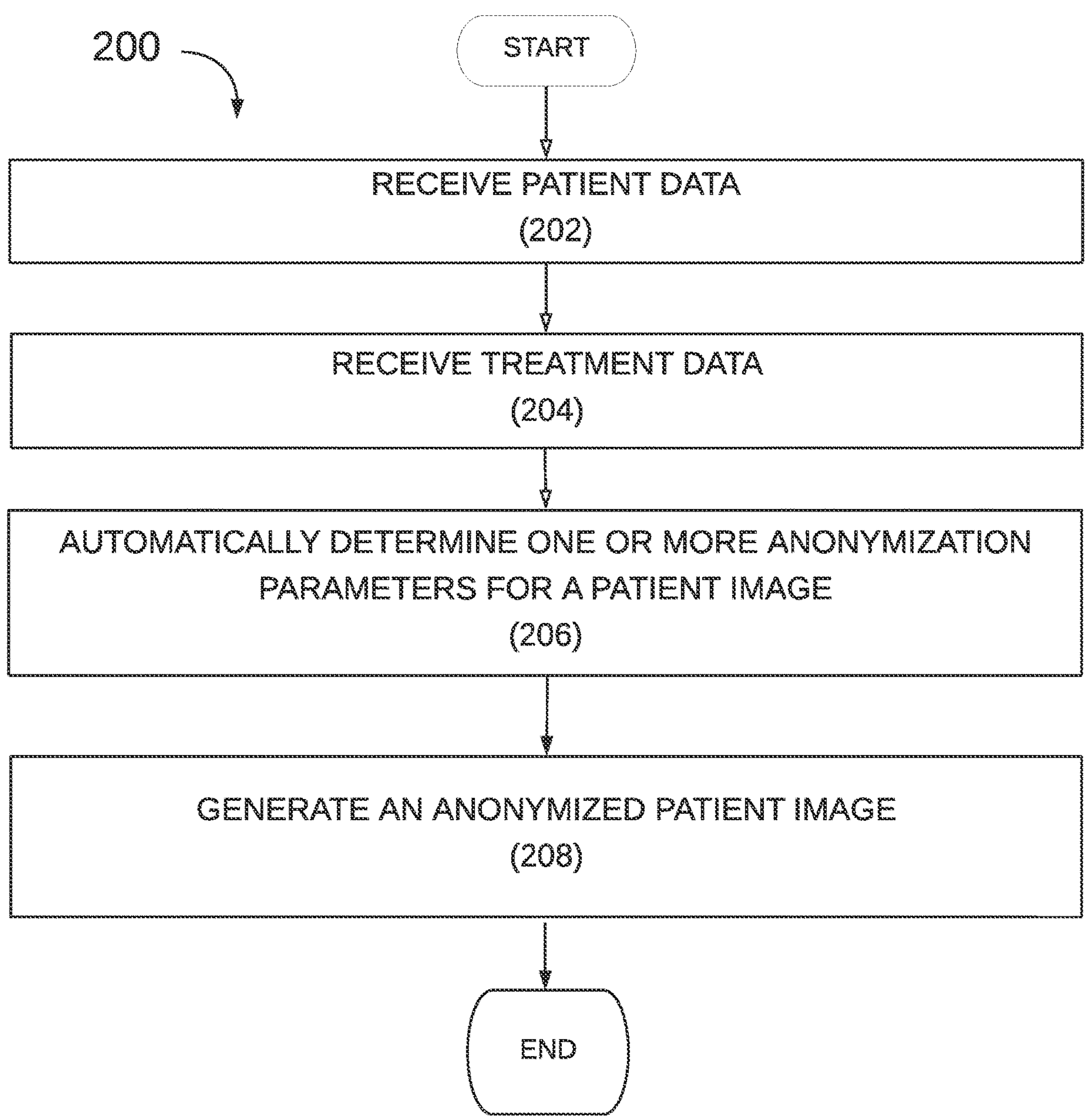

FIG. 2 illustrates a conceptual block diagram of an example process 200 for using semantic controls to anonymize patient data. Process 200 begins with step 202 in which patient data is received, e.g., by an anonymization system, such as system 100 discussed above with respect to FIG. 1. As discussed above, patient data can include virtually any type of information about a patient, including demographic information and/or patient images, such as digital images, videos and/or 3D scan data.

In step 204, the process 200 includes receiving treatment data, for example, that corresponds with a type of treatment administered to a patient associated with the received patient data (step 202). Treatment data can specify virtually any aspect of the administered clinical intervention, including but not limited to the identification of landmarks or regions of interest corresponding with different locations of the patient's anatomy, e.g., that are identified in image and/or 3D scan data of the patient.

In step 206, the process 200 includes automatically determining one or more anonymization parameters for a patient image, e.g., that is received as part of the patient data (step 202). As discussed above, the one or more anonymization parameters can be determined using semantic controls. For example, semantic controls (including various models and/ or application based rules), can be configured to ingest various inputs including but not limited to received patient data, received treatment data, and/or received user inputs, as described above with respect to FIG. 1.

At step 208, the process 200 can include generating an anonymized patient image, e.g., using the various semantic controls. The resulting image can include one that obfuscates various potentially aspects of a patient's appearance (e.g., to anonymize the patient image), while retaining clinically relevant visual features, for example, that demonstrate the outcome of a given clinical intervention. In some implementations, visual characteristics of the anonymized patient image may include global image changes, such as changes to the appearance of a patient's skin tone, or other modifications to change or alter aspects of the patient's demographic identity (e.g., the patient's gender). In other aspects, the anonymized image may include changes to specific image regions, e.g., that are identified by the anonymization parameters. By way of example, the anonymized patient image may include discrete image regions that have been altered (e.g., anonymization regions), while other regions are unaltered (e.g., clinically relevant regions), in order to convey clinically relevant information. Further details regarding the use of anonymization parameters to generate discrete anonymization/clinically relevant regions are discussed in further detail with respect to FIG. 3.

FIG. 3 illustrates a conceptual block diagram of an example process 300 for using semantic controls to anonymize patient data, e.g., by defining anonymization regions and clinically relevant regions of a patient image. As illustrated in FIG. 3, at step 302 one or more of the systems described herein (e.g., system 100 of FIG. 1) may receive patient data, including an input image, e.g., patient image (or representation data) 122.

At step 304, one or more of the systems described herein may identify key points, for example, that correspond to body landmarks. As discussed above, key points may be identified by anonymization parameters that are determined/identified using one or more semantic controls. By way of example, the key points may include key points that identify specific features or regions of the patient's anatomy, including but not limited to the eyebrows, eye opening or eyelids, the outline of the face, the jawline, the bridge, apex, nostrils, and/or ala of the nose, the mouth opening, the inside and outside of the lips, etc.

At step 306, one or more of the systems described herein may extract a clinically relevant sub-image. In some aspects, the clinically relevant sub-image can include regions of a patient image 122 that should not be modified, e.g., to maintain clinically relevant features or other information.

Figure 4:
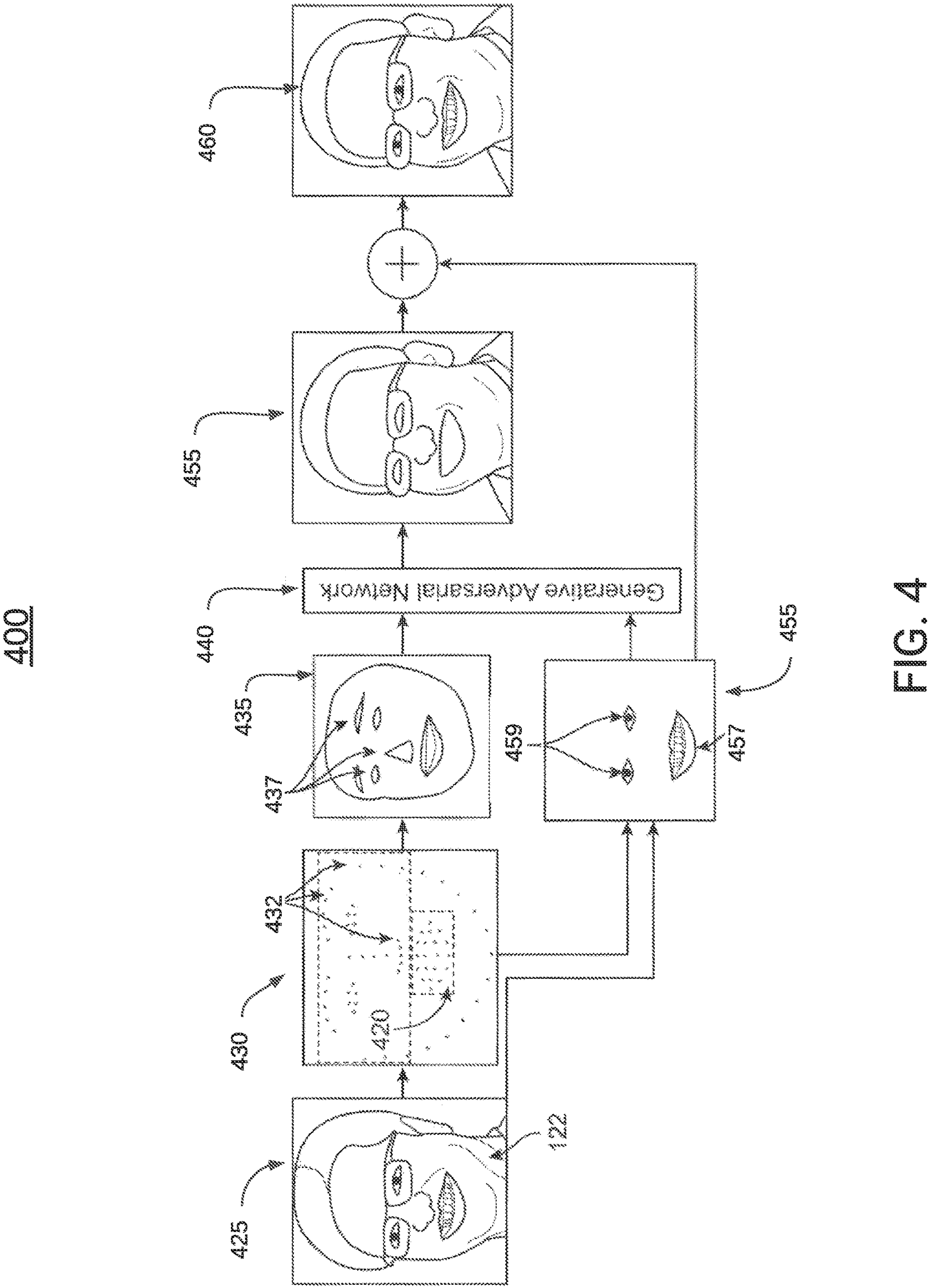
FIG. 4 is a flow diagram of an example process for anonymizing patient data, in accordance with some embodiments.

FIG. 4 shows a clinically relevant sub image 455 which includes a sub image of the mouth 457 and a sub image of the eyes 459. The sub images may be generated based on the key points. For example, sub image 457 may be generated based on the key points that define one or more of the mouth opening, inner edge of the lips, and the outer edge of the lips. A sub image may be generated based on a geometric shape generated by connecting the key points. In some embodiments, the sub image may include image data that extends beyond the key points or the geometric shape or area generated based on the key points. For example, the sub image may extend 1, 5, 10, 20, 50, or 100 pixels beyond the key points or the geometric shape or area generated based on the key points. In some embodiments, the sub image may extend beyond the key points a distance based on a dimension, such as a length or width of the geometric shape or area generated by the key points. For example, the sub image may extend about or less than about 1, 2, 5, 10, or 15 percent of the maximum liner dimension between two key points of the geometric shape or area generated based on the key points.

At step 308, one or more of the systems described herein may optionally create a structure image. FIG. 4 shows a structure image 435 generated based on the key points. The structure image 435 may include data representing one or more structures 437 of the face. For example, the structures 437 may represent the eyebrows, eyes, nose, mouth opening, lips, jawline, and face outline. The structures 437 may be based on the previously identified key points, for example, that are identified by anonymization parameters generated using one or more semantic controls. In some embodiments, the data represents a mask of the various features of a face. For example, structures 437 may include a mask of the outline of the face, a mask for the eyebrows, a mask for the eyes, a mask for the nose, a mask for the mouth opening, and a mask for the lips.

At step 310, one or more of the systems described herein may optionally create a color image. The color representation data can include aspects of the color of the image in the representation data. For example, the color representation data may include the colors in the image data and/or clinical representation data. In some embodiments, the color representation data may include the colors and the respective locations of the colors in the data. In some embodiments, the color representation data may include color of skin about the lips or eyes or color within the clinical data.

At step 312, one or more of the systems described herein may generate a new facial image. The generating module may include a generative machine learning model such as a generative adversarial network (GAN), such as GAN 440 of FIG. 4. In some embodiments, the generated artificial representation data may include image data, such as an image 455 that is generated based on the mask 435. In some embodiments, the image 455 is generated based on the mask 437 and the color data. In some embodiments, the artificial representation data may include data that artificially represents the representation data, without the representation data.

At step 314, one or more of the systems described herein may restore the clinically relevant sub-image to the new facial image. The clinical representation data may be incorporated into the artificial representation data based on the mask. For example, the mask may include data related to the relative positions of the artificial representation data and the clinical representation data. The anonymization system 100 may use the relative positions to position clinical representation data relative to the artificial representation data within an image, such as in image 460, which may be the anonymized representation data.

Figure 5:
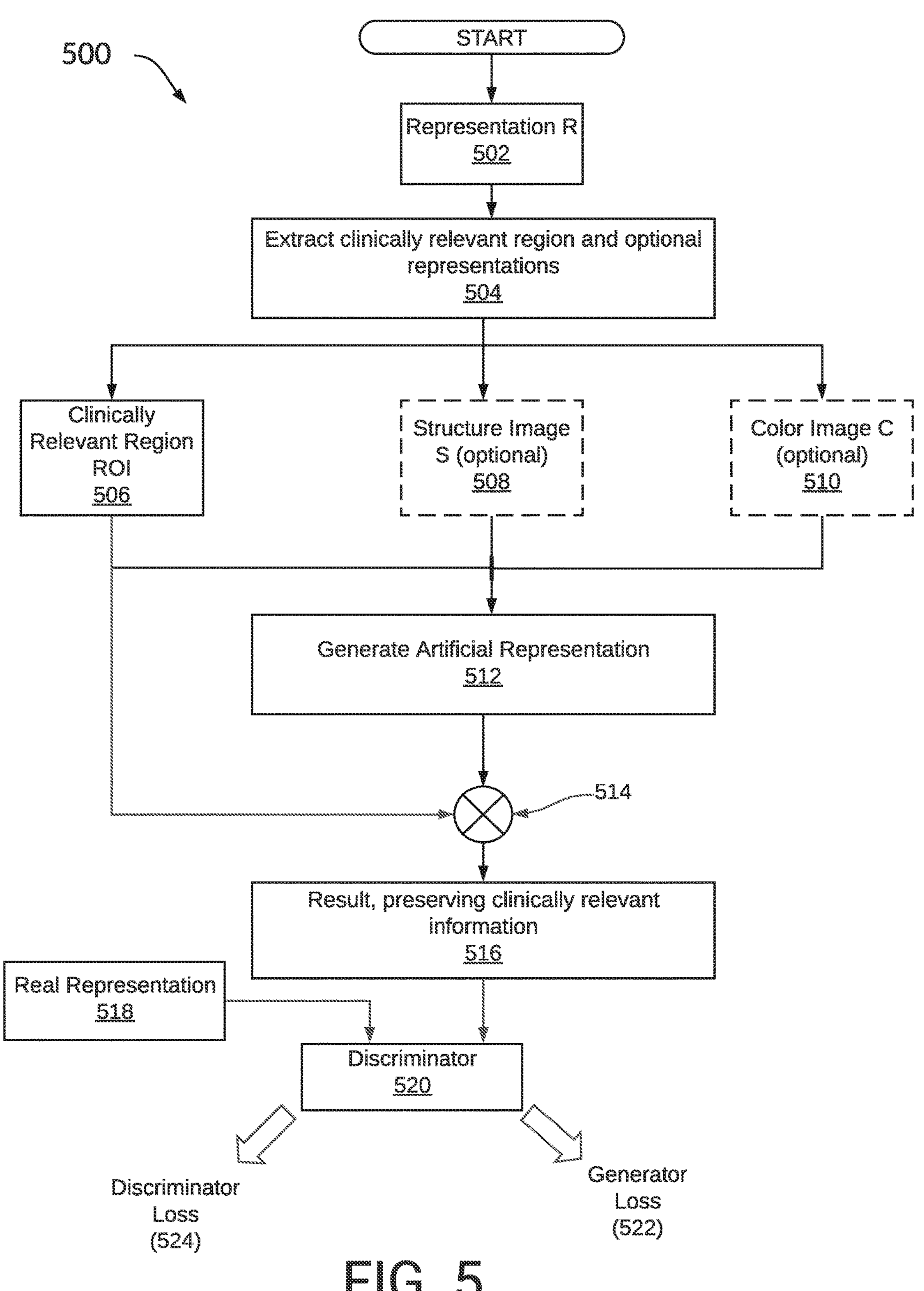
FIG. 5 illustrates an example of a dataflow diagram of an example computer-implemented dataflow for anonymizing patient data, in accordance with some examples.

FIG. 5 is a dataflow diagram of an example computer-implemented dataflow 500 for anonymizing clinical data. The steps shown in FIG. 5 may be performed by any suitable computer-executable code and/or computing system, including system 700 in FIG. 7, discussed below. In one example, each of the steps shown in FIG. 5 may represent an algorithm whose structure includes and/or is represented by multiple sub-steps, examples of which will be provided in greater detail below.

Dataflow 500 illustrates an example implementation utilizing a generative adversarial network (GAN). A GAN may utilize two separate machine learning (e.g., neural network) modules, a generator and a discriminator. The generator may be trained, using a dataset of relevant representation data (e.g., images), to generate realistic representation data of body parts. The generator may be further trained to reproduce the original representation data by determining a loss, using any appropriate loss function (e.g., L1 or Wasserstein), from the original representation data to the resulting representation data and back-propagating the gradient of the loss through the neural network. The back-propagation may adjust the neural network's parameters to minimize the loss.

A discriminator may process representation data to classify the input as "real" (e.g., appears genuine as if captured from the real world) or "generated" (e.g., appears to be artificially generated). The discriminator may be trained using datasets of known real representations and generated representations. The generator may then be trained to "fool" (e.g., have the discriminator classify a generated representation as a real representation) the discriminator. The discriminator's weights may be fixed such that the discriminator is not learning while training the generator. The error of fooling the discriminator (e.g., a negative of the discriminator loss) may be back-propagated through the generator to adjust the generator's weights in order to improve the realism of the generator's output. Further details regarding the implementation of various machine-learning approaches are discussed in relation to FIG. 6, below.

As illustrated in FIG. 5, at block 502, representation R, which may correspond to representation data, may be provided. At block 504, one or more of the systems described herein may extract a clinically relevant region and optional representations. As discussed above, the identified clinically relevant region and/or optional representations may be determined using one or more semantic controls. For example, the identified clinically relevant region and/or optional representations may be determined based on patient data, treatment data, and/or user inputs that have been ingest or otherwise exposed to one or more semantic controls, e.g., of an anonymization system 100, as discussed above with respect to FIGS. 1 and 2.

For example, an anonymization system (not illustrated) may, as part of computing device 700, be configured to extract clinically relevant region ROI, which may correspond to clinical representation data, from representation R at block 506. The extracting module may also optionally extract structure image S, which may correspond to a structure representation, from representation Rat block 508. The extracting module 106 may also optionally extract color image C, which may correspond to a color representation, from representation R at block 510.

At block 512, one or more of the systems described herein may generate an artificial representation, i.e., an anonymized version of the input patient image or 3D scan. For example, the anonymization system (not illustrated) may, as part of computing device 700, generate the artificial representation using clinically relevant region ROI, structure image S, and color image C as inputs. Subsequently, the artificial representation may be combined with clinically relevant region ROI with combinational operator 514, which may include, for instance, simple replacement, averaging values, alpha channel blurring, Gaussian alpha channel blurring, etc. The result, which preserves clinical information, at block 516 may anonymize the patient. The result may also fool the discriminator of the GAN.

FIG. 5 further illustrates an optional discriminative trainer portion. The result 516, as the result of the generator, may continue with a generator training path to discriminator 520, which may correspond to generating module 108. As described above, discriminator 520 may be trained, using discriminator loss 524. The generator may also be trained, via generator loss 522, to fool the discriminator.

In some implementations, the generator may be temporally aware in order to maintain temporal coherence for video or 3D video. For example, multiple frames of the source representation data and past reconstructed representations may be input into the generator. An additional discriminator may validate temporal coherence of the frames. Video may be generated by first creating a single frame and enforcing temporal coherence at subsequent times via the discriminator. Alternatively, the video may be generated from a single image and a series of poses. The generator may learn meta-information associated with modeling a pose into video. The generator may then generate a single image or 3D image, and represent that image transitioning through the series of poses using the meta-information.

In some implementations, before and after images may be created as short, two-frame video segments. The artificial representation data may remain constant for the two frames. The clinical representation data for before treatment and after treatment may then be embedded into or otherwise incorporated with the artificial representation data.

As explained above, a treatment professional may take photos of a patient's face and head. The anonymization methods and apparatus as described herein may receive the photos and identify the mouth for preservation. The anonymization methods and apparatus as described herein may artificially generate a face, which may look realistic and share non-identifiable features of the original face. The anonymization methods and apparatus may then embed the original mouth into the artificial face to create a realistic and aesthetically pleasing face. The anonymized face may maintain the mouth features for the treatment professional to observe, but may keep the patient's identity hidden. The anonymized face may preserve more information and be less distracting than conventional black-out or cropped facial images.

The anonymization methods and apparatus may be used to demonstrate smile examples or treatment planning examples. For instance, the anonymization methods and apparatus may support online smile galleries, be shown at dental conventions, be implemented as a mobile application, or be developed as a teaching tool.

The anonymization methods and apparatus may be used for researcher surveys. For example, consumers, general practitioners, and orthodontic professionals may be presented with anonymized photos to research smile properties (e.g., smile aesthetics, smile outcomes, etc.). The same smile may be presented in different facial contexts, such as across different ethnicities. Alternatively, the teeth may change (e.g., changing the midline, size of lateral incisor, etc.) and the face may stay the same.

Although the systems and methods are described above with respect to orthodontic treatment, in other implementations, the anonymization methods and apparatus may be used for other medical contexts, such as plastic surgery. Alternatively, the anonymization methods and apparatus may be used outside of medical contexts, such as for generating avatars, concealing minors' identities for publishing, etc. In such contexts, the clinically relevant region may correspond to or be defined by important body features relevant to the given context.

Figure 6:
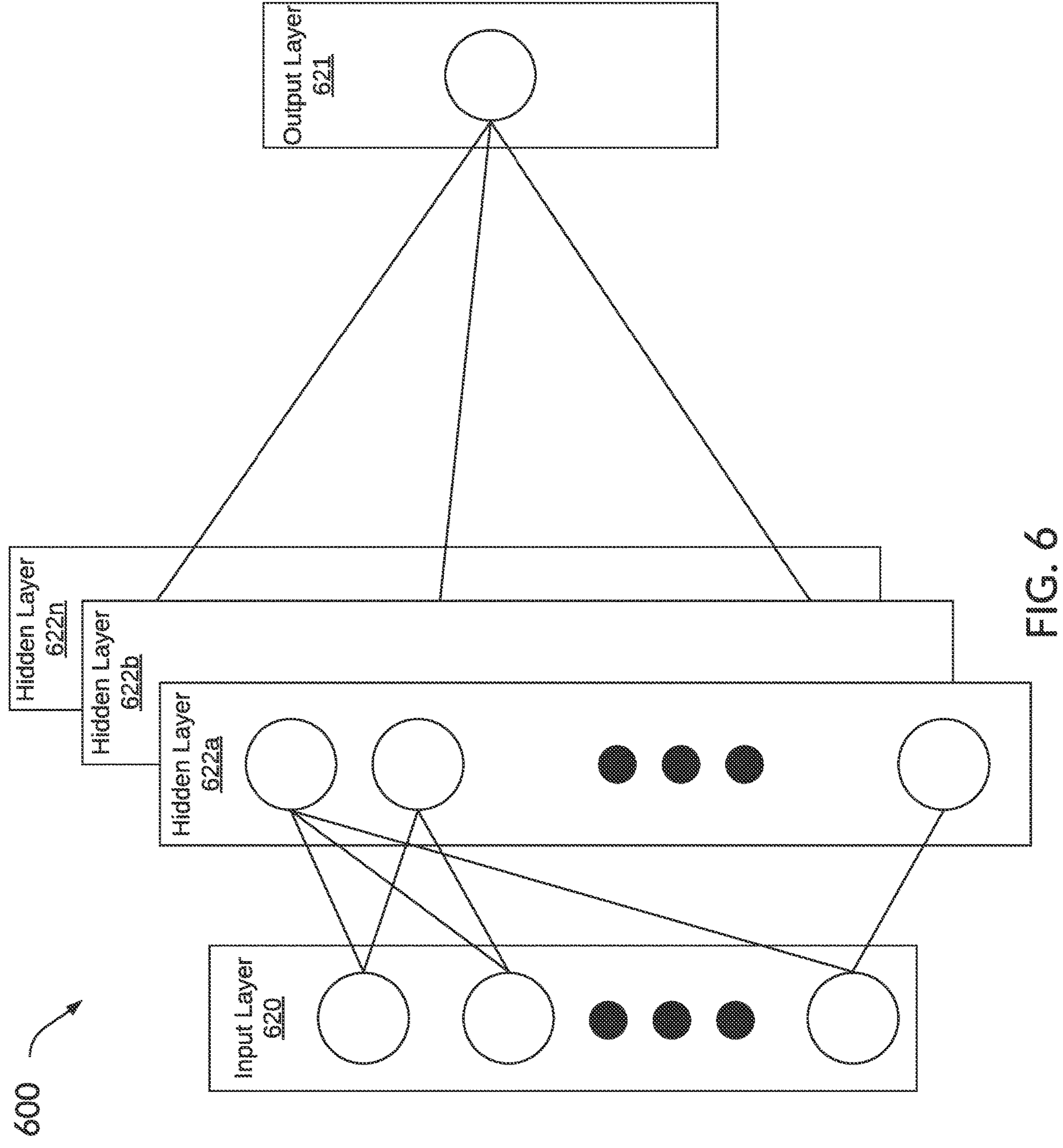
FIG. 6 illustrates an example of a deep learning neural network that can be implemented to facilitate a data de-identification process, in accordance with some examples.

The disclosure now turns to a further discussion of models that can be used through the environments and techniques described herein. Specifically, FIG. 6 is an illustrative example of a deep learning neural network 600 that can be implemented to facilitate a patient data anonymization process. The neural network 600 includes multiple hidden layers 622*a*, 622*b*, through 622*n*. The hidden layers 622*a*, 622*b*, through 622*n* include "n" number of hidden layers, where "n" is an integer greater than or equal to one. The number of hidden layers can be made to include as many layers as needed for the given application. The neural network 600 further includes an output layer 621 that provides an output resulting from the processing performed by the hidden layers 622*a*, 622*b*, through 622*n*. In one illustrative example, the output layer 621 can provide anonymized outputs, such as output images or 3D scans illustrating clinical outcomes of a patient. Notably, such outputs can be generated in a matter that obfuscates unique or identifying patient information.

The neural network 600 is a multi-layer neural network of interconnected nodes. Each node can represent a piece of information. Information associated with the nodes is shared among the different layers and each layer retains information as information is processed. In some cases, the neural network 600 can include a feed-forward network, in which case there are no feedback connections where outputs of the network are fed back into itself. In some cases, the neural network 600 can include a recurrent neural network, which can have loops that allow information to be carried across nodes while reading in input.

Information can be exchanged between nodes through node-to-node interconnections between the various layers. Nodes of the input layer 620 can activate a set of nodes in the first hidden layer 622*a*. For example, as shown, each of the input nodes of the input layer 620 is connected to each of the nodes of the first hidden layer 622*a*. The nodes of the first hidden layer 622*a* can transform the information of each input node by applying activation functions to the input node information. The information derived from the transformation can then be passed to and can activate the nodes of the next hidden layer 622*b*, which can perform their own designated functions. Example functions include convolutional, up-sampling, data transformation, and/or any other suitable functions. The output of the hidden layer 622*b* can then activate nodes of the next hidden layer, and so on. The output of the last hidden layer 622*n* can activate one or more nodes of the output layer 621, at which an output is provided. In some cases, while nodes (e.g., node 626) in the neural network 600 are shown as having multiple output lines, a node can have a single output and all lines shown as being output from a node represent the same output value.

In some cases, each node or interconnection between nodes can have a weight that is a set of parameters derived from the training of the neural network 600. Once the neural network 600 is trained, it can be referred to as a trained neural network, which can be used to classify one or more activities. For example, an interconnection between nodes can represent a piece of information learned about the interconnected nodes. The interconnection can have a tunable numeric weight that can be tuned (e.g., based on a training dataset), allowing the neural network 600 to be adaptive to inputs and able to learn as more and more data is processed.

The neural network 600 is pre-trained to process the features from the data in the input layer 620 using the different hidden layers 622*a*, 622*b*, through 622*n* in order to provide the output through the output layer 621.

In some cases, the neural network 600 can adjust the weights of the nodes using a training process called backpropagation. As noted above, a backpropagation process can include a forward pass, a loss function, a backward pass, and a weight update. The forward pass, loss function, backward pass, and parameter update is performed for one training iteration. The process can be repeated for a certain number of iterations for each set of training data until the neural network 600 is trained well enough so that the weights of the layers are accurately tuned.

As noted above, for a first training iteration for the neural network 600, the output will likely include values that do not give preference to any particular class due to the weights being randomly selected at initialization. For example, if the output is a vector with probabilities that the object includes different classes, the probability value for each of the different classes may be equal or at least very similar (e.g., for ten possible classes, each class may have a probability value of 0.1). With the initial weights, the neural network 600 is unable to determine low level features and thus cannot make an accurate determination of what the classification of the object might be. A loss function can be used to analyze error in the output. Any suitable loss function definition can be used, such as a Cross-Entropy loss. Another example of a loss function includes the mean squared error (MSE), defined as $E\_total=\Sigma(\frac{1}{2}(target-output)^2)$. The loss can be set to be equal to the value of E_total.

The loss (or error) will be high for the first training images since the actual values will be much different than the predicted output. The goal of training is to minimize the amount of loss so that the predicted output is the same as the training label. The neural network 600 can perform a backward pass by determining which inputs (weights) most contributed to the loss of the network, and can adjust the weights so that the loss decreases and is eventually minimized. A derivative of the loss with respect to the weights (denoted as dL/dW, where W are the weights at a particular layer) can be computed to determine the weights that contributed most to the loss of the network. After the derivative is computed, a weight update can be performed by updating all the weights of the filters. For example, the weights can be updated so that they change in the opposite direction of the gradient.

The neural network 600 can include any suitable deep network. One example includes a convolutional neural network (CNN), which includes an input layer and an output layer, with multiple hidden layers between the input and out layers. The hidden layers of a CNN include a series of convolutional, nonlinear, pooling (for downsampling), and fully connected layers. The neural network 600 can include any other deep network other than a CNN, such as an autoencoder, a deep belief nets (DBNs), a Recurrent Neural Networks (RNNs), among others.

As understood by those of skill in the art, machine-learning based classification techniques can vary depending on the desired implementation. For example, machine-learning classification schemes can utilize one or more of the following, alone or in combination: hidden Markov models; recurrent neural networks; convolutional neural networks (CNNs); deep learning; Bayesian symbolic methods; generative adversarial networks (GANs); support vector machines; image registration methods; applicable rule-based system. Where regression algorithms are used, they may include but are not limited to: a Stochastic Gradient Descent Regressor, and/or a Passive Aggressive Regressor, etc.

Machine learning classification models can also be based on clustering algorithms (e.g., a Mini-batch K-means clustering algorithm), a recommendation algorithm (e.g., a Miniwise Hashing algorithm, or Euclidean Locality-Sensitive Hashing (LSH) algorithm), and/or an anomaly detection algorithm, such as a Local outlier factor. Additionally, machine-learning models can employ a dimensionality reduction approach, such as, one or more of: a Mini-batch Dictionary Learning algorithm, an Incremental Principal Component Analysis (PCA) algorithm, a Latent Dirichlet Allocation algorithm, and/or a Mini-batch K-means algorithm, etc.

Figure 7:
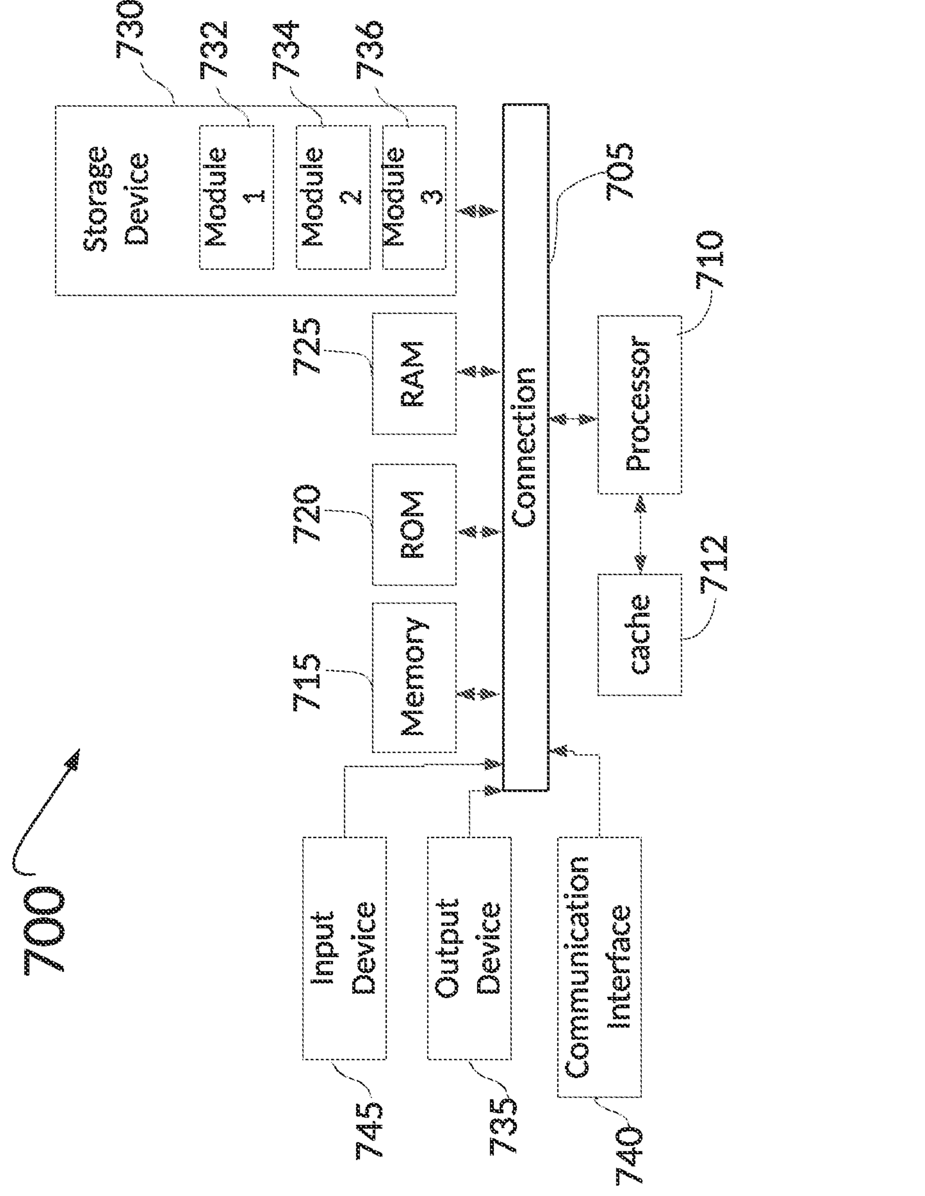
FIG. 7 illustrates an example computing system, in accordance with some examples.

The disclosure now turns to FIG. 7 which illustrates an example of a processor-based computing system 700 wherein the components of the system are in electrical communication with each other using a bus 705. The computing system 700 can include a processing unit (e.g., a CPU, GPU or/or processor) 710 and a system bus 705 that may couple various system components including the system memory 715, such as read only memory (ROM) 720 and random-access memory (RAM) 725, to the processor 710. The computing system 700 can include a cache 712 of high-speed memory connected directly with, in close proximity to, or integrated as part of the processor 710. The computing system 700 can copy data from the memory 715, ROM 720, RAM 725, and/or storage device 730 to the cache 712 for quick access by the processor 710. In this way, the cache 712 can provide a performance boost that avoids processor delays while waiting for data. These and other modules can control the processor 710 to perform various actions. Other system memory 715 may be available for use as well. The memory 715 can include multiple different types of memory with different performance characteristics. The processor 710 can include any general-purpose processor and a hardware module or software module, such as module 1 732, module 2 734, and module 3 736 stored in the storage device 730, configured to control the processor 710 as well as a special-purpose processor where software instructions are incorporated into the actual processor design. The processor 710 may essentially be a completely self-contained computing system, containing multiple cores or processors, a bus, memory controller, cache, etc. A multi-core processor may be symmetric or asymmetric.

To enable user interaction with the computing system 700, an input device 745 can represent any number of input mechanisms, such as a microphone for speech, a touch-protected screen for gesture or graphical input, keyboard, mouse, motion input, speech and so forth. An output device 735 can also be one or more of a number of output mechanisms known to those of skill in the art. In some instances, multimodal systems can enable a user to provide multiple types of input to communicate with the computing system 700. The communications interface 740 can govern and manage the user input and system output. There may be no restriction on operating on any particular hardware arrangement and therefore the basic features here may easily be substituted for improved hardware or firmware arrangements as they are developed.

The storage device 730 can be a non-volatile memory and can be a hard disk or other types of computer readable media which can store data that are accessible by a computer, such as magnetic cassettes, flash memory cards, solid state memory devices, digital versatile disks, cartridges, random access memory, read only memory, and hybrids thereof.

As discussed above, the storage device 730 can include the software modules 732, 734, 736 for controlling the processor 710. Other hardware or software modules are contemplated. The storage device 730 can be connected to the system bus 705. In some embodiments, a hardware module that performs a particular function can include a software component stored in a computer-readable medium in connection with the necessary hardware components, such as the processor 710, bus 705, output device 735, and so forth, to carry out the function. For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" refers to at least one of a set and indicates that one member of the set or multiple members of the set satisfy the claim. For example, claim language reciting "at least one of A and B" means A, B, or A and B.

What is claimed is:

1. A computer-implemented method comprising:

receiving patient data, wherein the patient data comprises a patient image corresponding with a patient;

receiving treatment data, wherein the treatment data is based on a treatment goal for the patient and specifies a clinical intervention to be performed on the patient, including portions of the patient's anatomy to be modified by the clinical intervention;

automatically determining, using one or more semantic controls, one or more anonymization parameters for the patient image based at least in part on the treatment data, wherein the one or more anonymization parameters define first pixel regions of the patient image that are to be altered, wherein the first pixel regions include one or more facial features;

generating, based on altering at least the first pixel regions of the patient image that are defined by the one or more anonymization parameters, an anonymized patient image, wherein the anonymized patient image:

comprises one or more modified facial features corresponding to the one or more facial features, wherein the one or more modified facial features comprise at least one of a modified skin color, a modified image geometry, or a modified prominence of at least one of the one or more facial features; and preserves one or more clinically relevant regions of the patient image in view of the treatment data, the one or more clinically relevant regions of the patient image comprising second pixel regions of the patient image depicting the portions of the patient's anatomy to be modified by the clinical intervention; and causing the anonymized patient image to be presented on a display device.

2. The computer-implemented method of claim 1, wherein the anonymized patient image preserves artifacts related to at least one of repositioning one or more teeth of the patient or repositioning jaw positions of the patient.

3. The computer-implemented method of claim 1, wherein the one or more anonymization parameters are further based on the patient data.

4. The computer-implemented method of claim 1, wherein the first pixel regions are to be modified to obfuscate an identity of the patient.

5. The computer-implemented method of claim 1, wherein the one or more anonymization parameters for the patient image specify the one or more clinically relevant regions in the patient image that are not to be modified in the patient image.

6. The computer-implemented method of claim 1, wherein the one or more anonymization parameters specify one or more image characteristics to be applied to generate the anonymized patient image.

7. The computer-implemented method of claim 6, wherein the one or more image characteristics include color parameters, blur filter parameters, geometric parameters, or a combination thereof.

8. The computer-implemented method of claim 1, wherein the one or more semantic controls are based on a user input.

9. The computer-implemented method of claim 1, wherein the anonymized patient image comprises global changes and changes to specific image regions of the patient image.

10. The computer-implemented method of claim 9, wherein the global changes comprise at least one of changes to skin color or changes that alter aspects of a demographic identity of the patient.

11. The computer-implemented method of claim 1, wherein generating the anonymized patient image comprises:

determining key points in the patient image that correspond to body landmarks;

generating a clinically relevant sub-image from the patient image based on the key points, the clinically relevant sub-image comprising the one or more clinically relevant regions of the patient image that are not to be modified, wherein the clinically relevant sub-image extends a specified number of pixels beyond the key points;

generating a color image from the patient image, the color image comprising color data for regions of the patient image;

processing the patient image and the color image using a generative machine learning model to output an initial anonymized patient image; and combining the initial anonymized patient image with the clinically relevant sub-image using at least one of replacement, averaging values, or alpha channel blurring.

12. The computer-implemented method of claim 11, wherein the generative machine learning model comprises a generative adversarial network (GAN).

13. A system, comprising:

at least one memory; and at least one processor coupled to the at least one memory, the at least one processor configured to:

receive patient data, wherein the patient data comprises a patient image corresponding with a patient;

receive treatment data, wherein the treatment data is based on a treatment goal for the patient and specifies a clinical intervention to be performed on the patient, including portions of the patient's anatomy to be modified by the clinical intervention;

automatically determine, using one or more semantic controls, one or more anonymization parameters for the patient image based at least in part on the treatment data, wherein the one or more anonymization parameters define first pixel regions of the patient image that are to be altered, wherein the first pixel regions include one or more facial features;

generate, based on altering at least the first pixel regions of the patient image defined by the one or more anonymization parameters, an anonymized patient image, wherein the anonymized patient image;

comprises one or more modified facial features corresponding to the one or more facial features, wherein the one or more modified facial features comprise at least one of a modified skin color, a modified image geometry, or a modified prominence of at least one of the one or more facial features; and preserves one or more clinically relevant regions of the patient image in view of the treatment data, the one or more clinically relevant regions of the patient image comprising second pixel regions of the patient image depicting the portions of the patient's anatomy to be modified by the clinical intervention; and cause the anonymized patient image to be presented on a display device.

14. The system of claim 13, wherein the one or more anonymization parameters are further based on the patient data.

15. The system of claim 13, wherein the first pixel regions are to be modified to obfuscate an identity of the patient.

16. The system of claim 13, wherein the one or more anonymization parameters for the patient image specify the one or more clinically relevant regions in the patient image that are not to be modified in the patient image.

17. The system of claim 13, wherein the one or more anonymization parameters specify one or more image characteristics to be applied to generate the anonymized patient image.

18. The system of claim 17, wherein the one or more image characteristics include color parameters, blur filter parameters, geometric parameters, or a combination thereof.

19. The system of claim 13, wherein the one or more semantic controls are based on a user input.

20. A non-transitory computer-readable storage medium comprising at least one instruction for causing a computer or processor to:

receive patient data, wherein the patient data comprises a patient image corresponding with a patient;

receive treatment data, wherein the treatment data is based on a treatment goal for the patient and specifies a clinical intervention to be performed on the patient, including portions of the patient's anatomy to be modified by the clinical intervention;

automatically determine, using one or more semantic controls, one or more anonymization parameters for the patient image based at least in part on the treatment data, wherein the one or more anonymization parameters define first pixel regions of the patient image that are to be altered, wherein the first pixel regions include one or more facial features;

generate, based on altering at least the first pixel regions of the patient image defined by the one or more anonymization parameters, an anonymized patient image, wherein the anonymized patient image:

comprises one or more modified facial features corresponding to the one or more facial features, wherein the one or more modified facial features comprise at least one of a modified skin color, a modified image geometry, or a modified prominence of at least one of the one or more facial features; and preserves one or more clinically relevant regions of the patient image in view of the treatment data, the one or more clinically relevant regions of the patient image comprising second pixel regions of the patient image depicting the portions of the patient's anatomy to be modified by the clinical intervention; and cause the anonymized patient image to be presented on a display device.

21. The non-transitory computer-readable storage medium of claim 20, wherein the one or more anonymization parameters are further based on the patient data.

22. The non-transitory computer-readable storage medium of claim 20, wherein the first pixel regions are to be modified to obfuscate an identity of the patient.

23. The non-transitory computer-readable storage medium of claim 20, wherein the one or more anonymization parameters for the patient image specify the one or more clinically relevant regions in the patient image that are not to be modified in the patient image.

24. The non-transitory computer-readable storage medium of claim 20, wherein the one or more anonymization parameters specify one or more image characteristics to be applied to generate the anonymized patient image.

25. The non-transitory computer-readable storage medium of claim 24, wherein the one or more image characteristics include color parameters, blur filter parameters, geometric parameters, or a combination thereof.

26. The non-transitory computer-readable storage medium of claim 20, wherein the one or more semantic controls are based on a user input.

* * * * *